US006863649B2

(12) United States Patent
Yasue

(10) Patent No.: US 6,863,649 B2
(45) Date of Patent: *Mar. 8, 2005

(54) EROGENIC ZONE STIMULATOR

(75) Inventor: Nobuhiro Yasue, Nakatsugawa (JP)

(73) Assignee: Toukaigikenkougyo Corporation, Gifu (JP)

( * ) Notice: Subject to any disclaimer, the term of this patent is extended or adjusted under 35 U.S.C. 154(b) by 18 days.

This patent is subject to a terminal disclaimer.

(21) Appl. No.: 10/257,968

(22) PCT Filed: Apr. 25, 2001

(86) PCT No.: PCT/JP01/03581

§ 371 (c)(1),
(2), (4) Date: Oct. 25, 2002

(87) PCT Pub. No.: WO01/82845

PCT Pub. Date: Nov. 8, 2001

(65) Prior Publication Data

US 2003/0092963 A1 May 15, 2003

(51) Int. Cl.[7] .................................................... A61F 5/00
(52) U.S. Cl. ........................................................ 600/38
(58) Field of Search ...................... 600/38–41; 604/201, 604/202, 191, 192, 193

(56) References Cited

U.S. PATENT DOCUMENTS

| | | | | | |
|---|---|---|---|---|---|
| 3,495,589 | A | | 2/1970 | Clement | |
| 3,741,216 | A | * | 6/1973 | Yosowitz et al. | 128/830 |
| 4,203,432 | A | | 5/1980 | Koch | |
| 4,960,113 | A | * | 10/1990 | Seeberg-Elverfeldt | 600/38 |
| D343,246 | S | | 1/1994 | Gaylor et al. | |
| D431,865 | S | | 10/2000 | Norton et al. | |
| 6,193,753 | B1 | | 2/2001 | Nordheim et al. | |
| 6,231,502 | B1 | | 5/2001 | McCarty | |
| 6,319,194 | B1 | | 11/2001 | Wulf | |
| 6,547,718 | B1 | * | 4/2003 | Yasue | 600/38 |

FOREIGN PATENT DOCUMENTS

| | | |
|---|---|---|
| JP | Y2-6-47455 | 12/1944 |
| JP | A-7-51312 | 2/1995 |
| JP | A-7-124188 | 5/1995 |
| JP | U-3033843 | 11/1996 |
| JP | U-3038874 | 4/1997 |
| JP | B1-3052961 | 4/2000 |

* cited by examiner

*Primary Examiner*—Samuel G. Gilbert
(74) *Attorney, Agent, or Firm*—Posz & Bethards, PLC

(57) ABSTRACT

A stimulating ring for giving a female sexual pleasure by stimulating a female sexual organ during intercourse. The stimulating ring (10) includes an inner ring (12) and an outer ring (14) made of silicone rubber. Both rings (12, 14) have U-shaped sections with thick walled portions (16, 20) formed at the ends of the U-shapes. During intercourse, the stimulating ring (10) is pressed from opposite sides and deformed, which causes the thick-walled portion (20) to stimulate a female vulva. In addition, a hollow structural body (40) which inflates inward in the radial direction of the ring is attached to the inner side of the inner ring (12) in a radial direction of the ring. It is possible to squeeze a root of a penis erected by a penis erection aiding tool, block the flow of the blood, and keep the penis congested by inflating the hollow structural body (40).

21 Claims, 16 Drawing Sheets

EROGENIC ZONE STIMULATOR

TECHNICAL FIELD

The present invention relates to a ring-shaped sexually sensitive portion stimulating tool which is fitted on a penis root.

BACKGROUND ART

This applicant previously filed an application of a sexually sensitive portion stimulating tool (sexually sensitive portion stimulating ring) capable of giving a female a feeling of sexual pleasure by stimulating a female sexual organ during sexual intercourse (Japanese patent Application No. H11-197758). This sexually sensitive portion stimulating tool is described below.

FIG. 13 is a side view of the sexually sensitive portion stimulating ring. FIG. 14 is a front view thereof. FIG. 15(a) is a sectional view taken along a line A—A of FIG. 13. FIG. 15(*b*) is a central cross-sectional view showing a state in which the sexually sensitive portion stimulating ring is pressed from opposite sides thereof.

As shown in FIGS. 13–15, a sexually sensitive portion stimulating ring 10 is constructed by fitting an outer ring 14 serving as a first ring on an inner ring 12 serving as a second ring.

The inner ring 12 is formed annularly from a molded material approximately U-shaped in section. The inner ring 12 is formed in its sectional configuration, as described below. That is, as shown in FIG. 15(*a*), the inner ring 12 is approximately U-shaped in section and has a concave portion (groove open in peripheral direction) 24 formed inside it. A pair of thick-walled portions (first displacement portion) 16 serving as a female sexual organ stimulating portion are formed at both tips of the approximately U-shaped inner ring 12. The thick-walled portion 16 is formed in the shape of an approximately square and projects inward. A curved portion 18 connecting the thick-walled portions 16 to each other and supporting the thick-walled portions 16 is formed between the thick-walled portions 16.

Similarly to the inner ring 12, the outer ring 14 is annularly formed from a molded material approximately U-shaped in section. The outer ring 14 is formed in its sectional configuration, as described below. That is, as shown in FIG. 15(*a*), a thick-walled portion (second displacement portion) 20 serving as a female sexual organ stimulating portion and an outer edge portion is formed at both tips of the U-shaped outer ring 14. The thick-walled portion 20 is approximately formed in the shape of a square and projects inward from a side surface of the outer ring 14. A curved portion 22 connecting both thick-walled portions 20 to each other is formed between both thick-walled portions 20. An inner surface of one thick-walled portion 20 and that of the other thick-walled portion 20 contact each other.

The thick-walled portion 20 positioned at the left side of FIG. 15(*a*) constitutes a first ring portion 20*a,* whereas the thick-walled portion 20 positioned at the right side constitutes a second ring portion 20*b.* The inner-side surface of the first ring portion 20*a* and that of the second ring portion 20*b* confront each other and are parallel with each other in the widthwise direction (left-to-right direction in FIG. 15(*a*) of the ring, namely, the axial direction thereof. The first and second ring portions 20*a,* 20*b* are supported by the curved portion 22 serving as a holding portion. The curved portion 22 is positioned at an inner peripheral side (radially inward) of the first and second ring portions 20*a,* 20*b* in the radial direction of the ring and constitutes a thin-walled portion thinner than the first and second ring portions 20*a,* 20*b*. The curved portion 22 supports the first and second ring portions 20*a,* 20*b* at a side surface thereof opposite to the confronting side surface thereof.

The inner diameter of the curved portion 22 of the outer ring 14 is formed a little larger than the inner diameter of the curved portion 18 of the inner ring 12. The outer ring 14 is fitted on the concave portion 24, approximately U-shaped in section and formed on the periphery of the inner ring 12. The thick-walled portion 16 of the inner ring 12 is spread by the outer ring 14, and the corner of the thick-walled portion 16 contacts a boundary portion between the thick-walled portion 20 of the outer ring 14 and the curved portion 22 thereof.

In this manner, an elastically deformable ring body having the outer ring 14 and the inner ring 12 is constructed. As shown in FIG. 2, the sexually sensitive portion stimulating ring 10 has a stepped construction. That is, when the sexually sensitive portion stimulating ring 10 is seen from the peripheral surface side thereof, the inner ring 12 is positioned at the outer side in the widthwise direction of the ring and the outer ring 14 is positioned at the inner side in the widthwise direction thereof, and the outer ring 14 is positioned outward beyond the inner ring 12 in the radial direction (vertical direction in FIG. 14) of the ring.

In the above-described sexually sensitive portion stimulating ring 10, both the inner ring 12 and the outer ring 14 are made of high quality silicone rubber, which has a hardness of 15–20° Hs, and are elastically deformable.

The sexually sensitive portion stimulating ring 10 is used as follows.

Initially, as shown in FIG. 16, the sexually sensitive portion stimulating ring 10 is fitted on the root of a penis I. In this state, the sexually sensitive portion stimulating ring 10 has an original shape, as shown in FIG. 15(*a*).

Then, the penis I is inserted into a vagina V to have a sexual intercourse, with the sexually sensitive portion stimulating ring 10 fitted on the root of the penis I. Thereupon, the side surface of the sexually sensitive portion stimulating ring 10 is pressed by male and female abdomens, with the sexually sensitive portion stimulating ring 10 sandwiched therebetween. Upon receipt of a pressure applied to the inner ring 12 from opposite sides thereof in the widthwise direction of the ring, the inner ring 12 is displaced elastically inward in the widthwise direction of the ring, and the corner of both thick-walled portions 16 of the inner ring 12 presses the boundary portion between the thick-walled portion 20 of the outer ring 14 and the curved portion 22 thereof.

At this time, the thick-walled portion 20 makes a rotary motion with an end, at the side of the curved portion 22, of the inner-side surface of the thick-walled portion 20 of the outer ring 14 operating as the supporting point. That is, the thick-walled portion 20 makes a motion of displacing toward the outer side in the widthwise direction of the ring, while the thick-walled portion 20 is displacing outward in the radial direction of the ring. In other words, the peripheral portion of the thick-walled portion 20 of the outer ring 14 in the radial direction of the ring makes a motion of spreading outward in the widthwise direction of the ring, with the inner peripheral portion of the thick-walled portion 20 in the radial direction of the ring serving as the supporting point. As a result, the thick-walled portion 20 of the outer ring 14 moves (displaces) outward in the widthwise direction of the ring.

As shown in FIG. 15(*b*), in this state, the thick-walled portion 20 of the outer ring 14 projects outward beyond the thick-walled portion 16 of the inner ring 12, whereas the curved portion 18 of the inner ring 12 flattens and projects inward. The curved portion 22 of the outer ring 14 is surrounded with the curved portion 18 of the inner ring 12. Accordingly, as shown in FIG. 16, the thick-walled portion 20 of the outer ring 14 contacts the female vulva C.

As described above, because the inner ring 12 is pressed in the widthwise direction of the ring, the thick-walled portion 16 of the inner ring 12 displaces inward elastically. With the displacement, the thick-walled portion 20 of the outer ring 14 displaces outward in the widthwise direction of the ring. Consequently, there is a change in the distance between the peripheral portion of the first ring portion 20*a* and that of the second ring portion 20*b* (between radially outward ends) in the radial direction of the ring.

When the pressure onto the inner ring 12 from its both side is released, the state shown in FIG. 15(*a*) is regained and the contact of the thick-walled portion 20 of the outer ring 14 with the vulva C of the female sexual organ is released.

Accordingly, during sexual intercourse the sexually sensitive portion stimulating ring 10 repeats the operation in which the thick-walled portion 20 of the outer ring 14 comes in contact with the vulva C of the female sexual organ and releases the contact, whereby the vulva C of the female sexual organ is stimulated.

Depending on relation in size between the inner diameter of the inner ring 12 and the penis, the root of the penis is squeezed with the curved portion 18 while in the state shown in FIG. 15(*b*) where the curved portion 18 of the inner ring 12 flattens and projects inward. The squeezing operation elongates the duration before ejaculation and is useful to males who suffer from premature ejaculation. Therefore, it is desirable for such males that the inner radius of the inner ring 12 is adjustable so that the squeezing operation works.

Though the sexually sensitive portion stimulating ring described above is useful for males with sufficient ability to erect, it is necessary for males without sufficient ability to erect to force their penis to elect and maintain its elected state by using a penis erection aiding tool in order to utilize the sexually sensitive portion stimulating ring.

A variety of penis erection aiding tools have been developed conventionally. The penis erection aiding tools are intended to accept insertion of a penis into its pipe-like receptacle, suck out and decompress air within the pipe-like receptacle (so-called vacuum pull), and turn the penis into congestion state by supplying it with blood. The applicant also filed that kind of penis erection tool previously. (Japanese Patent Application No.2000-102658). An abstract of the penis erection aiding tool is described below with reference to FIG. 17.

The penis erection aiding tool has a decompressing pipe 111 which is comprised of an outer pipe 111*a* that has an inner surface circular in section and an inner pipe 111*b* that also has an inner surface circular in section but is slightly smaller in diameter than the outer pipe 111*a*. The front edge of the inner pipe 111*b* forms an inserting mouth 119 into which a penis is inserted, and an air cushion 120 is fitted on it covering the entire circumference of the inner surface near the inserting mouth 119 as well as the entire circumference of the front edge. An air injection connector 122 for injecting air is installed at the air cushion 120. Furthermore, the back edge of the outer pipe 11*a* is blocked by a cap 115.

A pathway 125 which opens a path between the inside of the outer pipe 111*a* and the outside thereof is formed at the top face of the outer pipe 111*a*. A thick-walled portion 126 is formed surrounding the pathway 125, and forms a hollowed portion 128 which have an mouth open upward. A cylinder 140 circular in section stands vertically in the hollowed portion 128. An open mouth 141 which registers with the pathway 125 is formed at the bottom board 139 of the cylinder 140. A piston 142 is placed within the cylinder 140 so that the piston 142 can go up and down within the cylinder 140. A lever 145 is fixed to the top face of piston 142. The piston 142 slides in accordance with the vertical motion of the lever 145. The lower part of the cylinder 140 whose upper boundary lies at the piston 142 and the decompressing pipe 111 are together called a first air chamber (decompressing chamber) R1, and upper part of the cylinder 140 with its lower boundary at the piston 142 is called a second air chamber R2.

A pathway 148 which opens a path between the first air chamber R1 and the second air chamber R2 is formed at the piston 142. A packing 149 is fixed at upper opening of the pathway 148 on the top face of the piston 142 as a one-way valve. The packing 149 close the pathway 148 as the piston 142 moves upward, and allows the inflow of the air from the first air chamber R1 to the second air chamber R2 as it moves downward.

A hose 131 is attached to the second air chamber R2 of the cylinder 140 to open a path therefrom, and a nozzle 132 is installed on a tip of the hose 131.

The penis erection aiding tool constructed as above is used as follows.

Initially, a user fits a ring body 155 on the root of his own penis P, inserts the penis P from the inserting mouth 119, and adheres the ring body 155 to the air cushion. In addition, the user inserts the nozzle 132 into the air injection connector 156 of the ring body 155. Then at the stage where the ring body is pressed into the inserting mouth 119 the first air chamber R1 comes to an airtightness state.

The user pushes the lever 145 and makes the piston 142 advance downward. Then, in accordance with decrease of the volume of the first air chamber R1, the air in the first air chamber R1 passes through the pathway 148 of the piston 142, pushes up the packing 149, and moves to the second air chamber R2.

When the packing 149 moves down most and comes in contact with the bottom board 139, then the user pulls up the piston 142 and make it recede upward. Then, because the air in the second air chamber R2 is blocked by the packing 149, it does not move to the first air chamber R1, is ejected from the nozzle 132 into the ring body 155 through the horse 131, and makes the ring body 155 inflate. On the other hand, although the volume of the first air chamber R1 increases because of the upward receding of the piston 142, its interior comes to a decompressed state because no air inflows therein. Accordingly, blood flows into the penis P, the penis P congests, and an erection phenomenon occurs.

Next, the user pushes the lever 145 and makes the piston 142 advance downward. Afterwards, by repeating the push and pull of the lever 145 the decompress of the first air chamber R1 progresses and accordingly blood flows in furthermore and the penis P gradually erects as the ring body 155 inflates and decreases in its inner diameter. Thus, it becomes possible to block the flow of the blood which have flowed into the penis P and keep it congested.

Then, at the stage where desired erection is achieved and the ring body 155 is moderately squeezed, the nozzle 132 is detached from the air injection connector 156 of the ring body 155, the penis P is pulled out from the inserting mouth 119, and a sexual intercourse is initiated.

In addition, the ring body 155 can inflate not only by the supply of the compressed air from the hose 131 which opens a path to the second air chamber of the cylinder 140, but also by means of, in part, a pump which is prepared separately.

DISCLOSURE OF THE INVENTION

An object of the present invention is to provide a sexually sensitive portion stimulating tool which is obtained by improving the sexually sensitive portion stimulating tool the applicant previously filed.

Specifically, an object is to make the inner side in the ring's radial direction of the sexually sensitive portion stimulating tool variable in size.

In addition, an object is to use the sexually sensitive portion stimulating tool with the aforementioned penis erection aiding tool and replace the ring body 155 with the sexually sensitive portion stimulating tool the applicant previously filed.

In addition, an object is to prevent the outer ring and the inner ring from slipping off each other during sexual intercourse.

In addition, an object is to improve a feeling of sexual pleasure given to a female.

To achieve either of the above objects, the present invention has characteristics described in each item of the scope of claims.

Specifically, the sexually sensitive portion stimulating tool regarding the present invention includes an elastically deformable ring body, a first displacement portion which is provided on the ring body and is elastically displaced to an inner side in a widthwise direction of the ring body when the ring body is pressed in the widthwise direction of the ring body, and a second displacement portion which is provided on the ring body and is displaced to an outer side in the widthwise direction of the ring body with a displacement of the first displacement portion to the inner side in the widthwise direction of the ring body. The second displacement portion is constructed as a female sexual organ stimulating portion. Moreover, the sexually sensitive portion stimulating tool regarding the present invention includes a hollow structural body which is provided on the inner side of the ring body in a radial direction of the ring body and inflates inward in the radial direction of the ring body.

Owing to the above-described construction, with the displacement of the first displacement portion to the inner side in the widthwise direction of the ring, the second displacement portion serving as the female sexual organ stimulating portion displaces to the outer side in the widthwise direction of the ring. Therefore, during sexual intercourse, it is possible to give a feeling of sexual pleasure to a female. In addition, because the sexually sensitive portion stimulating tool includes the hollow structural body which is provided on the inner side of the ring body in a radial direction of the ring body and inflates inward in the radial direction of the ring body, it becomes possible to make the inner side in the ring's radial direction variable in size.

In this case, specifically, the second displacement portion makes an outward displacing motion in the widthwise direction of the ring body while the second displacement portion is displaced outwardly in a radial direction of the ring body. According to the invention specified in claim 3, a peripheral portion of the second displacement portion makes an outwardly spreading motion in the widthwise direction of the ring body, with an inner peripheral portion of the second displacement portion in the radial direction of the ring body serving as a supporting point.

The sexually sensitive portion stimulating tool regarding the present invention includes a ring body that is elastically deformable. The ring body has an inner ring, approximately U-shaped in section, having a groove open in a peripheral direction thereof; and an outer ring which has a female sexual organ stimulating portion and is fitted in the groove of the inner ring. When the inner ring deforms elastically upon receipt of a pressing force from opposite sides thereof in a widthwise direction of the ring body, the inner ring presses the outer ring, thus moving the female sexual organ stimulating portion. Moreover, the sexually sensitive portion stimulating tool has a hollow structural body which is provided on the inner side of the inner ring in a radial direction of the inner ring and inflates inward in the radial direction of the inner ring.

As described above, the inner ring deforms elastically upon receipt of the pressing force from the opposite sides thereof in the widthwise direction of the ring body, thus pressing the outer ring and moving the female sexual organ stimulating portion. Thus, during sexual intercourse, it is possible to give a female a feeling of sexual pleasure. In addition, because the ring body has a hollow structural body which is provided on the inner side of the inner ring in a radial direction of the inner ring and inflates inward in the radial direction of the inner ring, it becomes possible to make the inner side in the ring's radial direction variable in size.

The sexually sensitive portion stimulating tool regarding the present invention includes an outer ring, approximately U-shaped in section, which has a pair of thick-walled portions whose inner-side surfaces confront each other and a curved portion connecting both thick-walled portions to each other; and an inner ring, approximately U-shaped in section, having a groove open in a peripheral direction thereof. The outer ring is fitted in the groove of the inner ring. Upon receipt of a pressing force applied to an outer-side surface of the inner ring, both tips of the U-shaped inner ring press outer-side surfaces of both thick-walled portions of the outer ring to allow both thick-walled portions to make a rotary motion with an end at the side of the curved portion of an inner-side surface of each of both thick-walled portions of the outer ring operating as a supporting point so that both thick-walled portions stimulate a female sexual organ. Moreover, the sexually sensitive portion stimulating tool regarding the present invention includes a hollow structural body which is provided on the inner side of the inner ring in a radial direction of the inner ring and inflates inward in the radial direction of the inner ring.

As described above, upon receipt of the pressing force applied to the outer-side surface of the inner ring, both tips of the U-shaped inner ring press the outer-side surfaces of both thick-walled portions of the outer ring to allow each of both thick-walled portions to make a rotary motion with the end at the side of the curved portion of the inner-side surface of both thick-walled portions of the outer ring operating as the supporting point so that both thick-walled portions stimulate the female sexual organ. Therefore, during sexual intercourse it is possible to give a female a feeling of sexual pleasure. In addition, because the sexually sensitive portion stimulating tool has a hollow structural body which is provided on the inner side of the inner ring in a radial direction of the inner ring and inflates inward in the radial direction of the inner ring, it becomes possible to make the inner side in the ring's radial direction variable in size.

In this case, a positioning member for keeping the outer ring having a constant distance with respect to the inner ring is provided inside the groove of the inner ring. In this case, even though the outer ring is dislocated from the inner ring in the radial direction of the ring, the outer ring can immediately return to the right position with respect to the inner ring. The positioning member can be unitedly formed with the outer ring.

If a groove for forming an air hole communicating with a space formed of both thick-walled portions described above and the curved portion and with the outside of each other is formed on an inner-side surface of each of the thick-walled portions, then, during sexual intercourse, it is possible to return both thick-walled portions quickly from the outwardly displaced state to the original state and operate both thick-walled portions properly. In addition, by making each one of the thick walled portions constructed so that a radius is formed on the inner-side end and the outer-side end thereof in the radial direction of the ring, it becomes able to prevent a female having a feeling of physical disorder.

The sexually sensitive portion stimulating tool regarding the present invention includes an outer ring whose outer edge serves as a female sexual organ stimulating portion, and an inner ring whose side surface receives a pressing force. The sexually sensitive portion stimulating tool has a stepped construction in such a way that when the sexually sensitive portion stimulating tool is seen from a peripheral surface side thereof, the inner ring is positioned at an outer side in a widthwise direction of the sexually sensitive portion stimulating tool and the outer ring is positioned at an inner side in the widthwise direction thereof, and the outer ring is positioned outward beyond the inner ring in a radial direction of the sexually sensitive portion stimulating tool to form a stepped construction. The female sexual organ stimulating portion is displaced outward in the widthwise direction of the sexually sensitive portion stimulating tool upon receipt of a pressing force applied to the side surface of the inner ring and stimulates a female sexual organ. Moreover, the sexually sensitive portion stimulating tool regarding the present invention includes a hollow structural body which is provided on the inner side of the inner ring in a radial direction of the inner ring and inflates inward in the radial direction of the inner ring.

As described above, the female sexual organ stimulating portion displaces outward in the widthwise direction of the sexually sensitive portion stimulating tool upon receipt of the pressing force applied to the side surface of the inner ring and stimulates the female sexual organ. Therefore, during sexual intercourse, it is possible to give a female a feeling of sexual pleasure. In addition, because the sexually sensitive portion stimulating tool has a hollow structural body which is provided on the inner side of the inner ring in a radial direction of the inner ring and inflates inward in the radial direction of the inner ring, it becomes possible to make the inner side in the ring's radial direction variable in size.

The sexually sensitive portion stimulating tool regarding the present invention includes a ring body having a first ring portion, a second ring portion parallel with the first ring portion in a widthwise direction of the sexually sensitive portion stimulating tool, and an elastically deformable holding portion for holding the first and second ring portions. The ring body is so formed that the distance between a peripheral portion of the first ring portion and that of the second ring portion in a radial direction of the ring body is varied by a change in a pressing force applied to a side surface of the ring body. Moreover, the sexually sensitive portion stimulating tool regarding the present invention includes a hollow structural body which is provided on the inner side of the inner ring in the radial direction of ring body and inflates inward in the radial direction of the ring body.

As described above, in the ring body having the first ring portion, the second ring portion, and the holding portion, the ring body is so formed that the distance between the peripheral portion of the first ring portion and that of the second ring portion in the radial direction of the sexually sensitive portion stimulating tool is varied by a change in the pressing force applied to the side surface of the sexually sensitive portion stimulating tool. Thus, the operation of the first ring portion or that of the second ring portion is capable of giving a female a feeling of sexual pleasure during sexual intercourse. In addition, because the sexually sensitive portion stimulating tool regarding the present invention includes a hollow structural body which is provided on the inner side of the inner ring in the radial direction of the ring body and inflates inward in the radial direction of the ring body, it becomes possible to make the inner side in the ring's radial direction variable in size.

In this case, specifically, the ring-shaped sexually sensitive portion stimulating tool can be constructed so that the holding portion is positioned at an inner peripheral side of the first and second ring portions in the radial direction of the sexually sensitive portion stimulating tool and supports the first and second ring portions at a thin-walled portion thereof thinner than the first and second ring portions, and so that the thin-walled portion supports the first and second ring portions at a side surface thereof opposite to confronting side surfaces of the first and second ring portions.

The hollow structural body described above can be made to inflate by injection of air. In addition, it becomes easy to inject the air into the hollow structural body if a hose which has an air injecting portion is attached to the hollow structural body.

The hollow structural body described above can be attached to the ring body (the inner ring) releasably as well as fixedly beforehand as in the embodiment to be described later.

The ring-shaped sexually sensitive portion stimulating tool regarding the present invention includes a ring body that is elastically deformable. The ring body has an inner ring, approximately U-shaped in section, having a groove open in a peripheral direction thereof; and an outer ring which has a female sexual organ stimulating portion and is fitted in the groove of the inner ring. When the inner ring deforms elastically upon receipt of a pressing force from opposite sides thereof in a widthwise direction of the ring body, the inner ring presses the outer ring, thus moving the female sexual organ stimulating portion. Moreover the sexually sensitive portion stimulating tool regarding the present invention includes a slipping off preventing member which is provided on the both outer side of the outer ring in the widthwise direction of the ring body and contacts with the outermost circumferential portion of the inner ring.

As described above, the inner ring deforms elastically upon receipt of the pressing force from the opposite sides thereof in the widthwise direction of the ring body, thus pressing the outer ring and moving the female sexual organ stimulating portion. Thus, during sexual intercourse, it is possible to give a female a feeling of sexual pleasure. In addition, because the sexually sensitive portion stimulating tool regarding the present invention includes a slipping off preventing member which is provided on the both outer side of the outer ring in the widthwise direction of the ring body and contacts with the outermost circumferential portion of the inner ring, it becomes possible to prevent the outer ring and the inner ring from slipping off each other during sexual intercourse.

The sexually sensitive portion stimulating tool regarding the present invention includes an outer ring, approximately U-shaped in section, which has a pair of thick-walled portions whose inner-side surfaces confront each other and a curved portion connecting both thick-walled portions to each other; and an inner ring, approximately U-shaped in section, having a groove open in a peripheral direction thereof. The outer ring is fitted in the groove of the inner ring. Upon receipt of a pressing force applied to an outer-side surface of the inner ring, both tips of the U-shaped inner ring press outer-side surfaces of both thick-walled portions of the outer ring to allow both thick-walled portions to make a rotary motion with an end at the side of the curved portion of an inner-side surface of each of both thick-walled portions of the outer ring operating as a supporting point so that both thick-walled portions stimulate a female sexual organ. Moreover the sexually sensitive portion stimulating tool regarding the present invention includes a slipping off preventing member which is provided on the both outer side of the outer ring in the widthwise direction of the sexually sensitive portion stimulating tool and contacts with the outermost circumferential portion of the inner ring.

As described above, upon receipt of the pressing force applied to the outer-side surface of the inner ring, both tips of the U-shaped inner ring press the outer-side surfaces of both thick-walled portions of the outer ring to allow each of both thick-walled portions to make a rotary motion with the end at the side of the curved portion of the inner-side surface of both thick-walled portions of the outer ring operating as the supporting point so that both thick-walled portions stimulate the female sexual organ. Therefore, during sexual intercourse it is possible to give a female a feeling of sexual pleasure. In addition, because the sexually sensitive portion stimulating tool regarding the present invention includes a slipping off preventing member which is provided on the both outer side of the outer ring in the widthwise direction of the sexually sensitive portion stimulating tool and contacts with the outermost circumferential portion of the inner ring, it becomes possible to prevent the outer ring and the inner ring from slipping off each other during sexual intercourse.

In this case, when a positioning member for keeping the outer ring having a constant distance with respect to the inner ring is provided inside the groove of the inner ring, even though the outer ring is dislocated from the inner ring in the radial direction of the ring, the outer ring can immediately return to the right position with respect to the inner ring. This slipping off preventing member can be unitedly formed with the outer ring.

The sexually sensitive portion stimulating tool regarding the present invention includes an outer ring whose outer edge serves as a female sexual organ stimulating portion, and an inner ring whose side surface receives a pressing force. The sexually sensitive portion stimulating tool has a stepped construction in such a way that when the sexually sensitive portion stimulating tool is seen from a peripheral surface side thereof, the inner ring is positioned at an outer side in a widthwise direction of the sexually sensitive portion stimulating tool and the outer ring is positioned at an inner side in the widthwise direction thereof, and the outer ring is positioned outward beyond the inner ring in a radial direction of the sexually sensitive portion stimulating tool to form a stepped construction. The female sexual organ stimulating portion is displaced outward in the widthwise direction of the sexually sensitive portion stimulating tool upon receipt of a pressing force applied to the side surface of the inner ring and stimulates a female sexual organ. Moreover the sexually sensitive portion stimulating tool regarding the present invention includes a slipping off preventing member which is provided on the both outer side of the outer ring in the widthwise direction of the sexually sensitive portion stimulating tool and contacts with the outermost circumferential portion of the inner ring.

As described above, the female sexual organ stimulating portion displaces outward in the widthwise direction of the sexually sensitive portion stimulating tool upon receipt of the pressing force applied to the side surface of the inner ring and stimulates the female sexual organ. Therefore, during sexual intercourse, it is possible to give a female a feeling of sexual pleasure. In addition, because the sexually sensitive portion stimulating tool regarding the present invention includes a slipping off preventing member which is provided on the both outer side of the outer ring in the widthwise direction of the sexually sensitive portion stimulating tool and contacts with the outermost circumferential portion of the inner ring, it becomes possible to prevent the outer ring and the inner ring from slipping off each other during sexual intercourse.

If a circular salient is formed on the both outer side of the outer ring in the widthwise direction of the sexually sensitive portion stimulating tool and the slipping off preventing members are formed on the inner side of the circular salients in the radial direction thereof, it becomes easier to make the inner ring displace during sexual intercourse and furthermore the slipping off preventing members are positioned on the inner side of the circular salients in the widthwise direction thereof, and thus it becomes possible to improve a feeling of sexual pleasure given to a female.

And it is preferable that the sexually sensitive portion stimulating tool regarding the present invention includes a ring-shape keeping member in the outer ring. Using a spring free at its both ends as the ring-shape keeping member, it becomes possible to deform the outer ring and the inner ring moderately.

And it becomes possible for the inner ring to regain its original state quickly from the state in which it displaces during sexual intercourse if air holes are formed between the outer ring and the inner ring.

BEST MODE FOR CARRYING OUT THE INVENTION

Figure 1B:
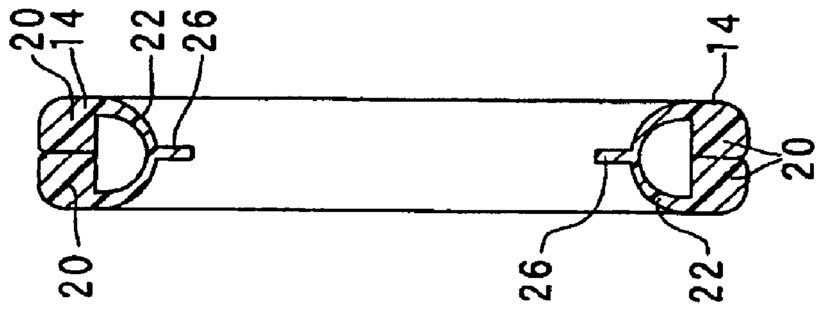
FIG. 1 shows a configuration of a sexually sensitive portion stimulating ring of the first embodiment of the present invention.

The embodiments of the present invention will be described with reference to drawings. In the embodiments described below, elements which have the same reference numerals as those in FIG. 13–FIG. 16 has are the same or almost the same as those in FIG. 13–FIG. 15, respectively.

(First Embodiment)

Figure 13:
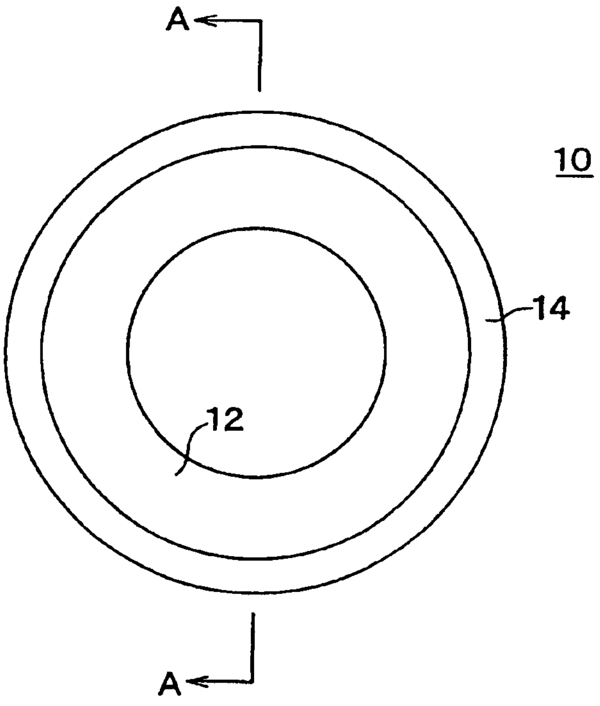
FIG. 13 PRIOR ART
FIG. 13 is a side view of the sexually sensitive portion stimulating tool the applicant previously filed.
Figure 14:
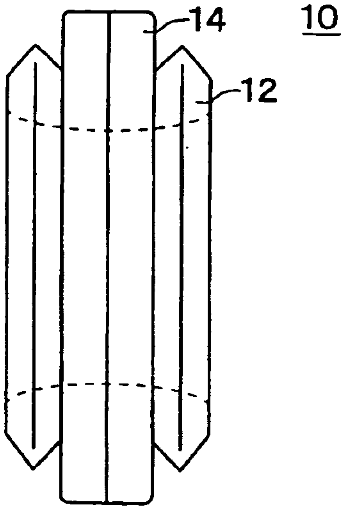
FIG. 14 PRIOR ART
FIG. 14 is a front view of the sexually sensitive portion stimulating tool shown in FIG. 13.
Figure 15A:
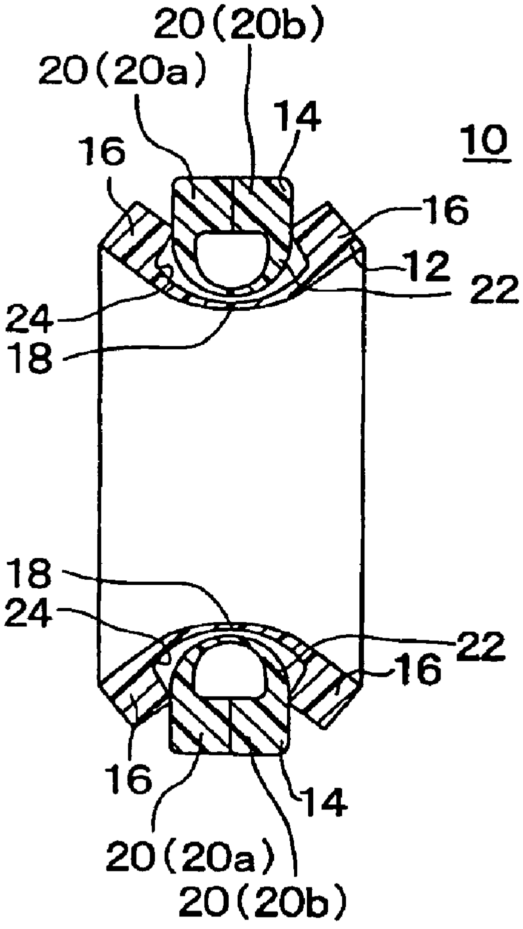
FIG. 15(a) PRIOR ART
FIG. 15(*a*) is a sectional view taken along a line A—A of FIG. 13, and FIG. 15(*b*) is a central cross-sectional view of a state in which the sexually sensitive portion stimulating ring shown in FIG. 13 is pressed from opposite sides thereof.
Figure 15B:
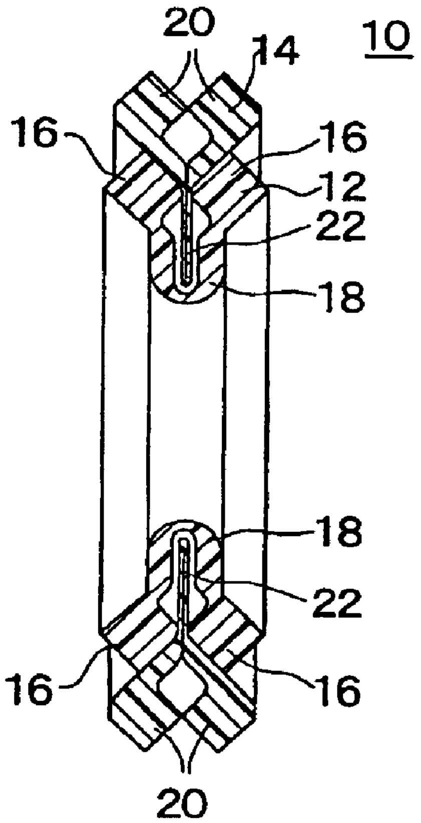
FIG. 15(b) PRIOR ART
Figure 16:
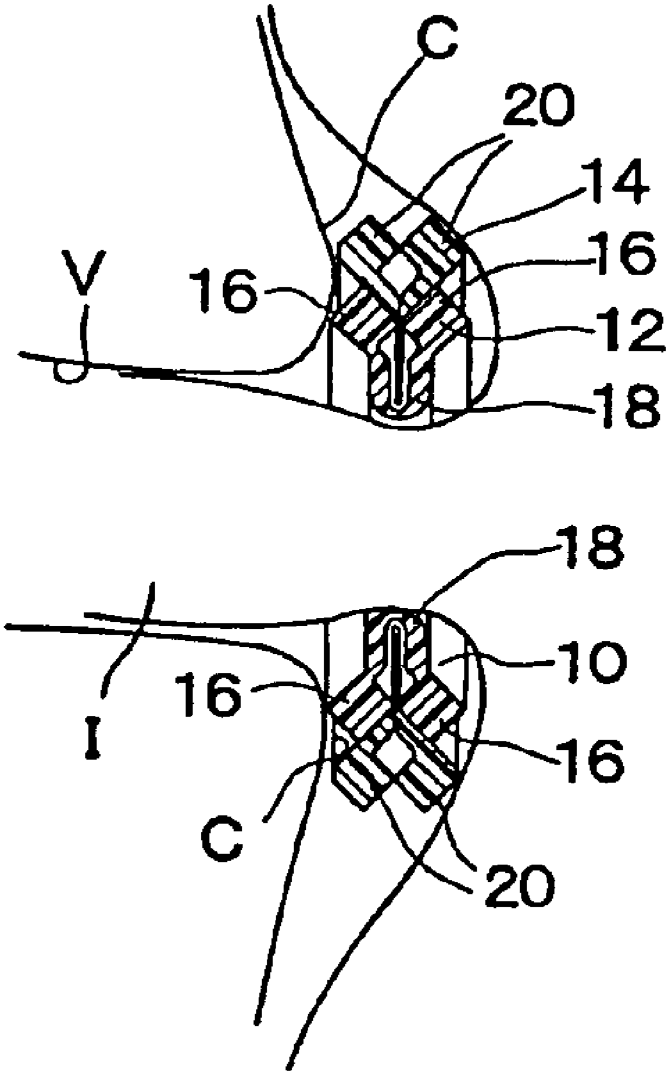
FIG. 16 PRIOR ART
FIG. 16 is a sectional view of a state in which the sexually sensitive portion stimulating ring shown in FIG. 13 is used.

Because the fundamental configuration of a sexually sensitive portion stimulating ring 10 according to the embodiment is basically same as the one which is shown in FIG. 13–FIG. 15, its parts which differ from the ones in FIGS. 13–15 will mainly be described.

Figure 1A:
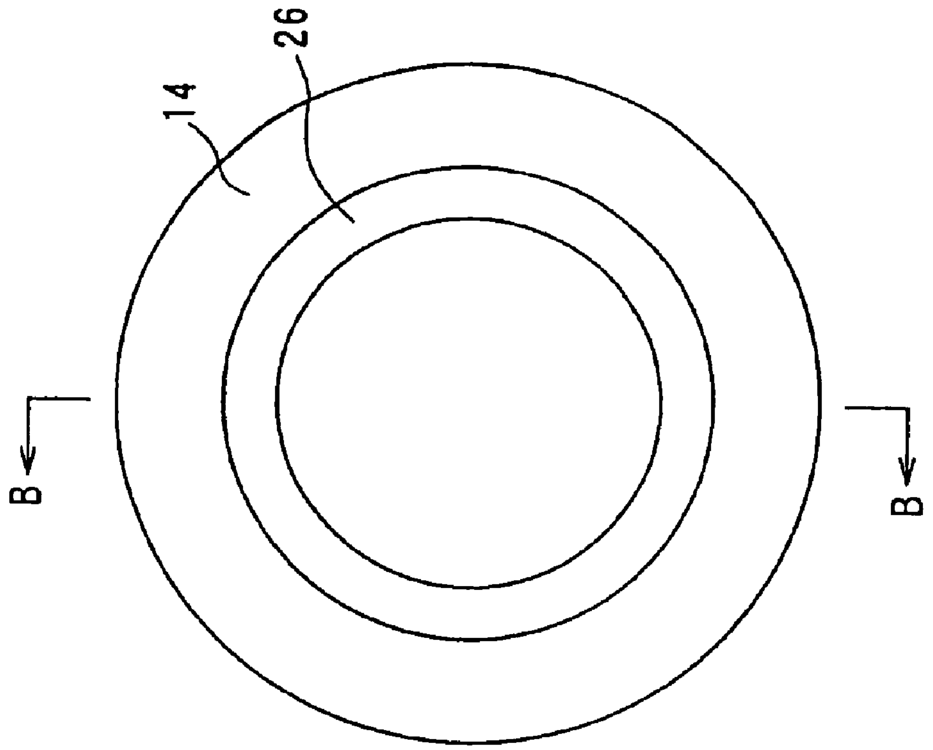
Figure 2A:
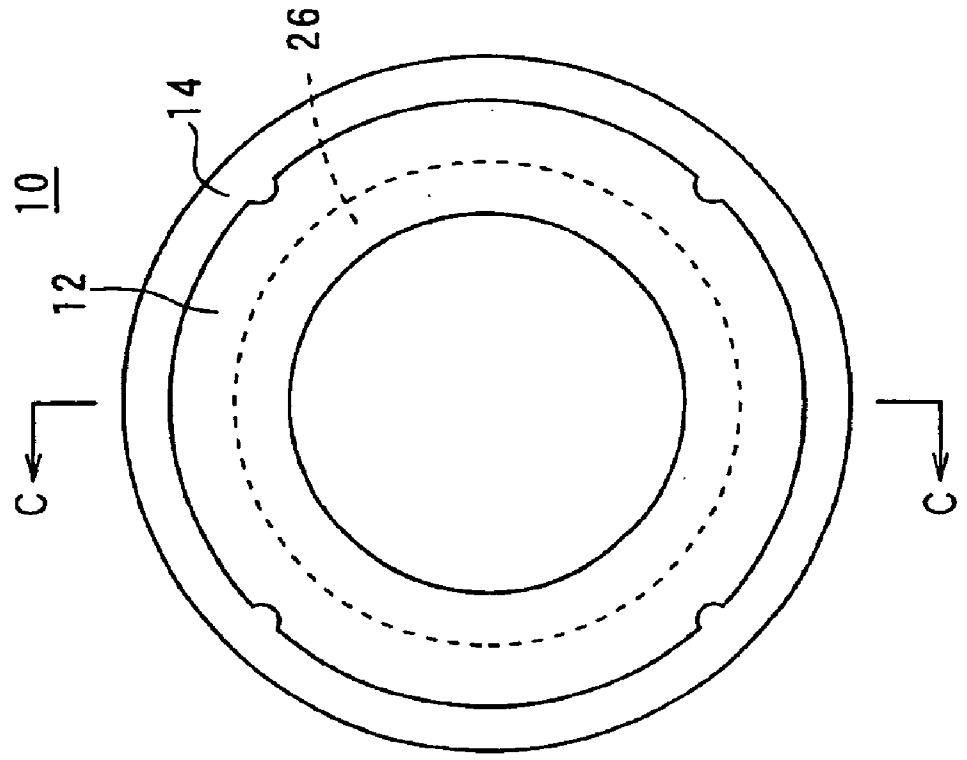
FIG. 2 shows a state in which the outer ring is fitted on an inner ring for the first embodiment of the sexually sensitive portion stimulating ring.
Figure 2B:
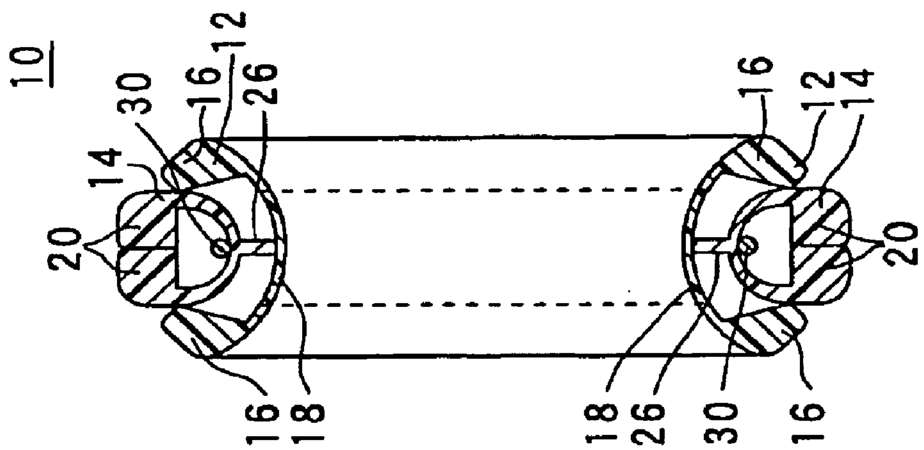

FIG. 1 shows a configuration of an outer ring 14 of the embodiment. FIG. 1(*a*) is a side view of the outer ring 14, and FIG. 1(*b*) is a sectional view taken along the line B—B of FIG. 1(*b*). FIG. 2 shows a state in which the outer ring 14 is fitted on an inner ring 12. FIG. 2(*a*) is a side view of the state, FIG. 2(*b*) is a sectional view taken along the line C—C. It should be noted that a hollow structural body to be described below is not installed in this figure.

In the embodiment, as shown in FIG. 1, the outer ring 14 is formed so that a radius is formed on the inner-side end (namely, the end, at the opposite side of the curved portion 22, of the inner-side surface of the thick-walled portion 20 of the outer ring 14) and the outer-side end, in the radial direction of the ring, of the peripheral portion of the thick-walled portion 20 in the widthwise direction of the ring. The thick-walled portion 20 of the outer ring 14 contacts the female vulva during sexual intercourse. However, if the outer surface of the thick-walled portion 20 of the outer ring 14 is angular, the female has a feeling of physical disorder. Thus, all the corners of the outer surface of the thick-walled portion 20 of the outer ring 14 are rounded in the embodiment, resulting in the prevention of the female having a feeling of physical disorder.

Figure 3A:
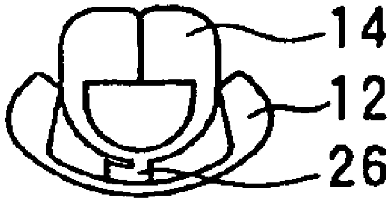
FIG. 3 shows a state in which the outer ring returns to its proper position with respect to the ring quickly even if the outer ring slipped off the inner ring towards the radial direction of the ring.
Figure 3B:
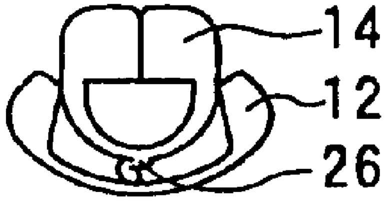
Figure 3C:
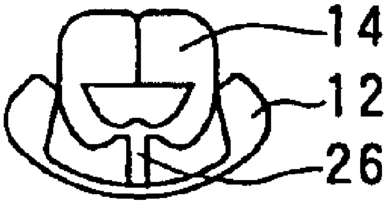

A projection 26 is formed integrally with the curved portion 22 of the outer ring 14 such that the projection 26 is disposed on the inner side of the ring in the radial direction thereof. As shown in FIG. 2, with the outer ring 14 fitted on the inner ring 12, the projection 26 operates as a positioning member for keeping the outer ring 14 having a constant distance with respect to the inner ring 12. That is, if the projection 26 is not formed, during the sexual intercourse, the outer ring 14 remains dislocated from the inner ring 12 in the radial direction of the ring. Consequently, a situation that the thick-walled portion 20 of the outer ring 14 does not operate properly may occur. However, by forming the projection 26, even though the outer ring 14 is dislocated from the inner ring 12 in the radial direction of the ring, the outer ring 14 can return immediately to the right position with respect to the inner ring 12. That is, as shown in FIG. 3(*a*), when the outer ring 14 is dislocated from the inner ring 12 in the radial direction of the ring, the projection 26 deforms and operates in a direction in which the deformation is released. Therefore, the state of the projection 26 changes from that shown in FIG. 3(*b*) to that shown in FIG. 3(*c*). In this manner, the projection 26 is capable of returning the outer ring 14 to the right position with respect to the inner ring 12.

Figure 4C:
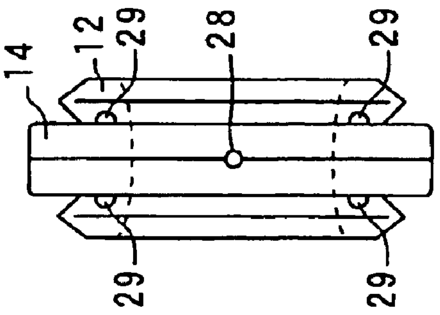
FIG. 4 shows a configuration on an inner-side surface of a thick-walled portion of each the outer ring and the inner ring and an air hole formed on the outer ring and the inner ring.
Figure 4B:
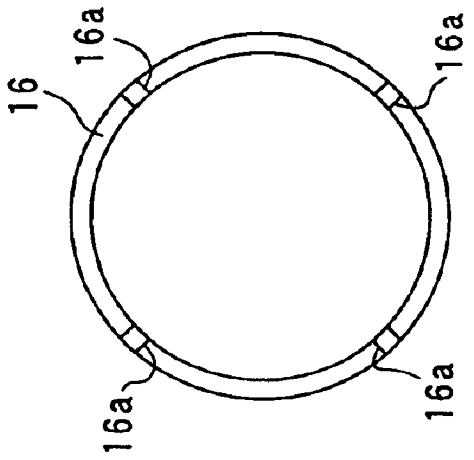
Figure 4A:
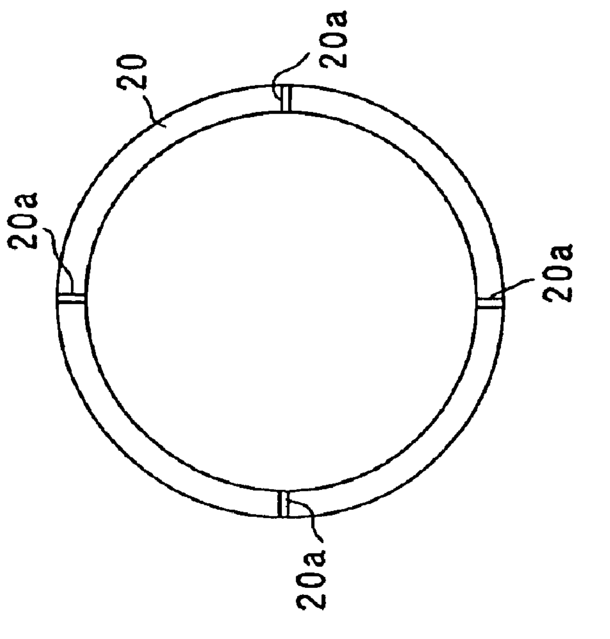

In the embodiment, as shown in FIG. 4(*a*), a groove 20*a* is formed, on several point symmetric positions, for example on upper, lower, left, and right positions, of the inner-side surface of each thick-walled portion 20 of the outer ring 14. And as shown in FIG. 4(*b*), a groove 16*a* is formed, on several point symmetric positions, for example on upper, lower, left, and right positions, of the inner-side surface of each thick-walled portion 16 of the inner ring 14. With the outer ring 14 fitted on the inner ring 12 and with the inner-side surfaces of both thick-walled portions 20 in contact each other, as shown in FIG. 4(*c*), the groove 20*a* allows formation of an air hole 28 communicating with the outside and an inner space formed of the thick-walled portion 20 and the curved portion 22 of the outer ring 14 and the thick-walled portion 20 with each other. And as shown in FIG. 4(*c*), the groove 16*a* allows formation of an air hole 29 communicating with the outside and an inner space formed of the thick-walled portion 16 and the curved portion 18 of the inner ring 12 and the thick-walled portion 20 of the outer ring 14.

By forming the air holes 28 and 29, during sexual intercourse, it is possible to quickly return both thick-walled portions 20 and 16 from the outwardly displaced state to the original state and operate both thick-walled portions 20 properly. It should be noted that because sexually sensitive portion stimulating ring 10 is constructed by fitting the outer ring 14 on the inner ring 12, relative arrangement between the air hole 28 and 29 varies depending on how the outer ring 14 is fitted on the inner ring.

Figure 5A:
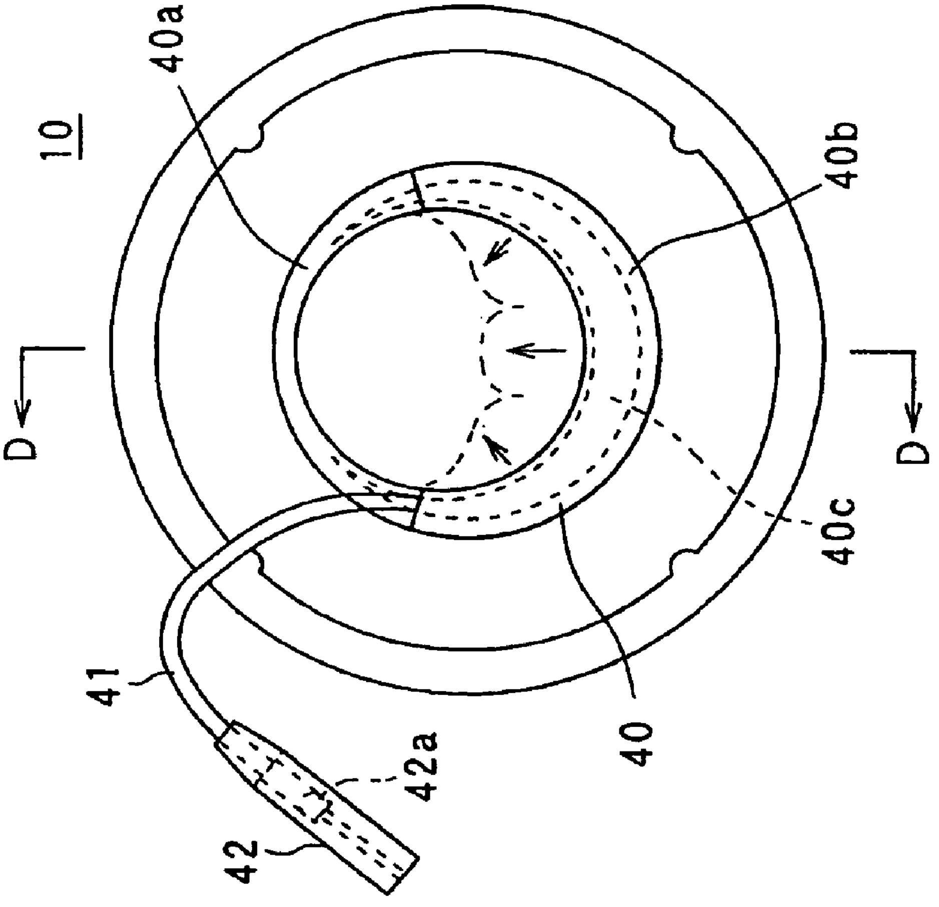
FIG. 5 shows a state in which the outer ring is fitted on an inner ring and a hollow structural body is fitted on the inner side of the inner ring in the radial direction of the ring.
Figure 5B:
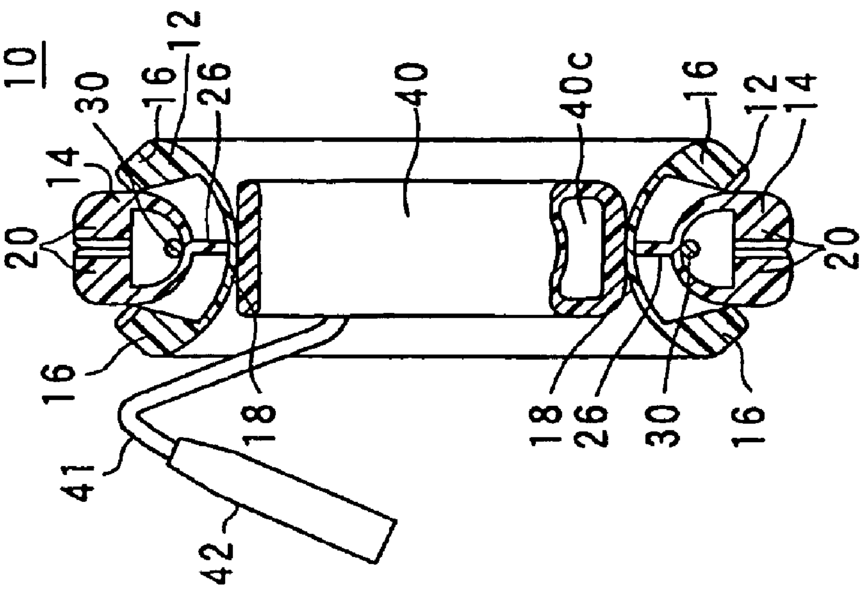

In the embodiment, in the state where the outer ring 14 is fitted on the inner ring 12, a bag-shaped hollow structural body 40 is attached to the inside of the inner ring 12 in the radial direction thereof, as shown in FIG. 5. The hollow structural body 40 is formed of a material body (for example, elastic member like silicone rubber) which is hollow in its interior and inflates inward in the radial direction of the ring by injection of air. The hollow 40*c* of the hollow structural body 40 varies its own cross section section by section as shown in FIG. 5, and not installed to entire inner circumference of the inner ring 12. Accordingly, it is possible to make the hollow structural body inflate inward in the radial direction of the ring by injection of air. The hollow structural body 40 is to be attached by inserting, in other words, it is detachable from the inner ring 12.

A hose 41 is attached to the hollow structural body 40 for injecting the air into its interior. The hollow structural body 40 is comprised of two members 40*a* and 40*b*, and is constructed by inserting, bonding, and fixing one member 40*a* to the other member 40*b* at their both ends, and the hollow structural body which has the hose 41 is constructed by inserting, bonding, and fixing one member 40*a* to the other member 40*b* along with the hose 41*a* at one of the ends of the both member 40*a* and 40*b*.

An air injection member 42 is formed at the end of the hose 41. This air injection member 42 has a one-way valve (air valve), which only allows supply of air toward the hollow structural body.

Figure 6:
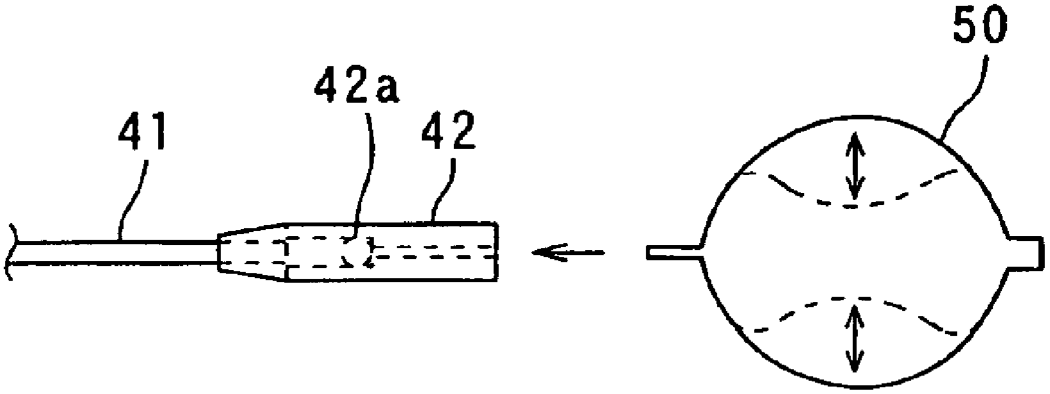
FIG. 6 shows a state in which an air pump is attached to an air injection portion of the hollow structural body.

An air pump 50 is installed releasably to the air injection member 42 of the hollow structural body 40 as shown in FIG. 6. In the state where the air pump 50 is attached, when the air pump 50 is treated to deform vertically (direction of the vertical arrows in the figure) to inject air, the interior of the hollow structural body is provided with the air from the air pump 50 through the air injection member 42 and the hose 41. By the supply of the air, the hollow structural body 40 inflate inward in the radial direction of the ring as shown by the arrows in FIG. 5 and comes to a state shown by the broken line in FIG. 5.

In the embodiment, as shown in FIG. 2, a ring-shape keeping member (for example, ring-shaped member made of a wire, a spring, or the like) 30 which keeps ring's shape circular is fitted on the outer ring 12. This ring-shape keeping member 30 is used to prevent the outer ring 14 and the inner ring 12 from deforming and to keep the outer ring 14 and inner ring 12 circular in shape when the hollow structural body 40 inflates.

The sexually sensitive portion stimulating ring 10 (in the state shown in FIG. 5) constructed as above is used as follows.

Initially, a user fits the sexually sensitive portion stimulating ring 10 in the state shown in FIG. 5 on the root of his own penis. In this state, his penis is not erecting sufficiently. Then, with the penis erection aiding tool shown in FIG. 17 (the hose 131 is detached because ejection of the air to the ring body 155 is not done), the user inserts his penis into the decompression pipe 111, sucks out and decompresses the air within the decompression pipe 111 (so-called vacuum pull), and turns his penis into congestion state by supplying it with blood. Then, in the state where sufficient erection is achieved, the user sends the air to the hollow structural body 40 by the pump 50 through the air injection member 42 and hose 41 and make the hollow structural body 40 inflate. Accordingly, the sexually sensitive portion stimulating ring 10 can decrease in its inner diameter and block the flow of the blood which have flowed into the penis P and keep it congested.

Afterward, the user pulls his penis out of the penis erection aiding tool and starts sexual intercourse. During the sexual intercourse, the sexually sensitive portion stimulating ring 10 operates basically in the same way as shown in FIG. 13–FIG. 15.

Thus, the side surface of the sexually sensitive portion stimulating ring 10 is pressed by male and female abdomens, with the sexually sensitive portion stimulating ring 10 sandwiched therebetween. Upon receipt of a pressure applied to the inner ring 12 from opposite sides thereof in the widthwise direction of the ring, the inner ring 12 is displaced elastically inward in the widthwise direction of the ring, and the corner of both thick-walled portions 16 of the inner ring 12 presses the boundary portion between the thick-walled portion 20 of the outer ring 14 and the curved portion 22 thereof. At this time, the thick-walled portion 20 makes a rotary motion with an end, at the side of the curved portion 22, of the inner-side surface of the thick-walled portion 20 of the outer ring 14 operating as the supporting point. That is, the thick-walled portion 20 makes a motion of displacing toward the outer side in the widthwise direction of the ring, while the thick-walled portion 20 is displacing outward in the radial direction of the ring. In other words, the peripheral portion of the thick-walled portion 20 of the outer ring 14 in the radial direction of the ring makes a motion of spreading outward in the widthwise direction of the ring, with the inner peripheral portion of the thick-walled portion 20 in the radial direction of the ring serving as the supporting point. As a result, the thick-walled portion 20 of the outer ring 14 moves (displaces) outward in the widthwise direction of the ring and comes in contact with the female vulva.

As described above, because the inner ring 12 is pressed in the widthwise direction of the ring, the thick-walled portion 16 of the inner ring 12 displaces inward elastically. With the displacement, the thick-walled portion 20 of the outer ring 14 displaces outward in the widthwise direction of the ring. Consequently, there is a change in the distance between the peripheral portion of the first ring portion 20*a* and that of the second ring portion 20*b* (between radially outward ends) in the radial direction of the ring.

Accordingly, during sexual intercourse the sexually sensitive portion stimulating ring 10 repeats the operation in which the thick-walled portion 20 of the outer ring 14 comes in contact with the vulva of the female sexual organ and releases the contact, whereas the vulva of the female sexual organ is stimulated.

Figure 17:
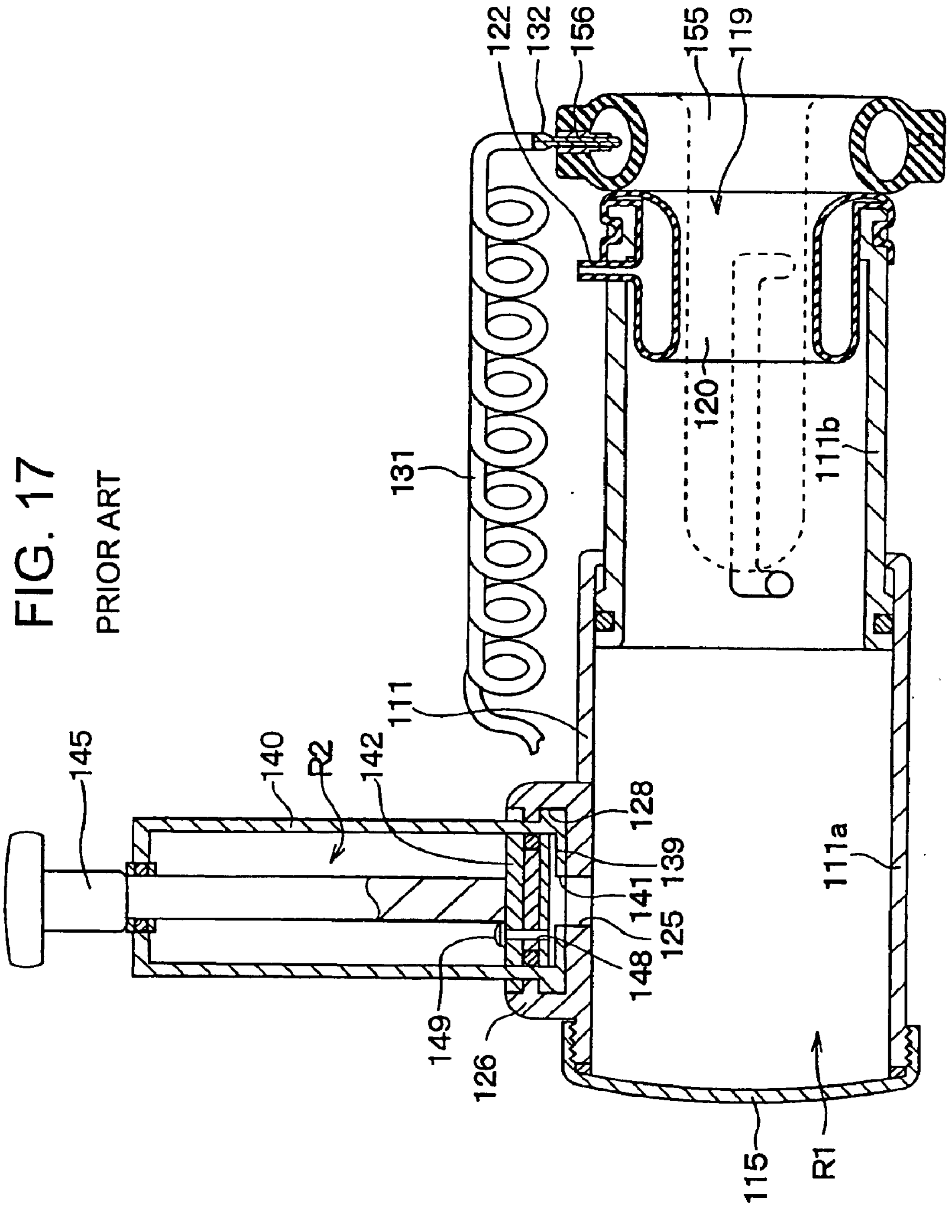
FIG. 17 PRIOR ART
FIG. 17 shows a configuration of the penis erection aiding tool the applicant previously filed.

In addition, the sexually sensitive portion stimulating ring 10 described above can be used along with a penis erection aiding tool other than the one shown in FIG. 17.

Moreover, the sexually sensitive portion stimulating ring 10 described above can be used efficiently without being used along with such a penis erection aiding tool. It is able to adjust the inner diameter of the inner ring 12 by the inflation of the hollow structural body 40 and thus add squeezing operation during sexual intercourse. The squeezing operation elongates the duration before ejaculation and is useful to males who suffer from premature ejaculation.

(Second Embodiment)

Figure 7:
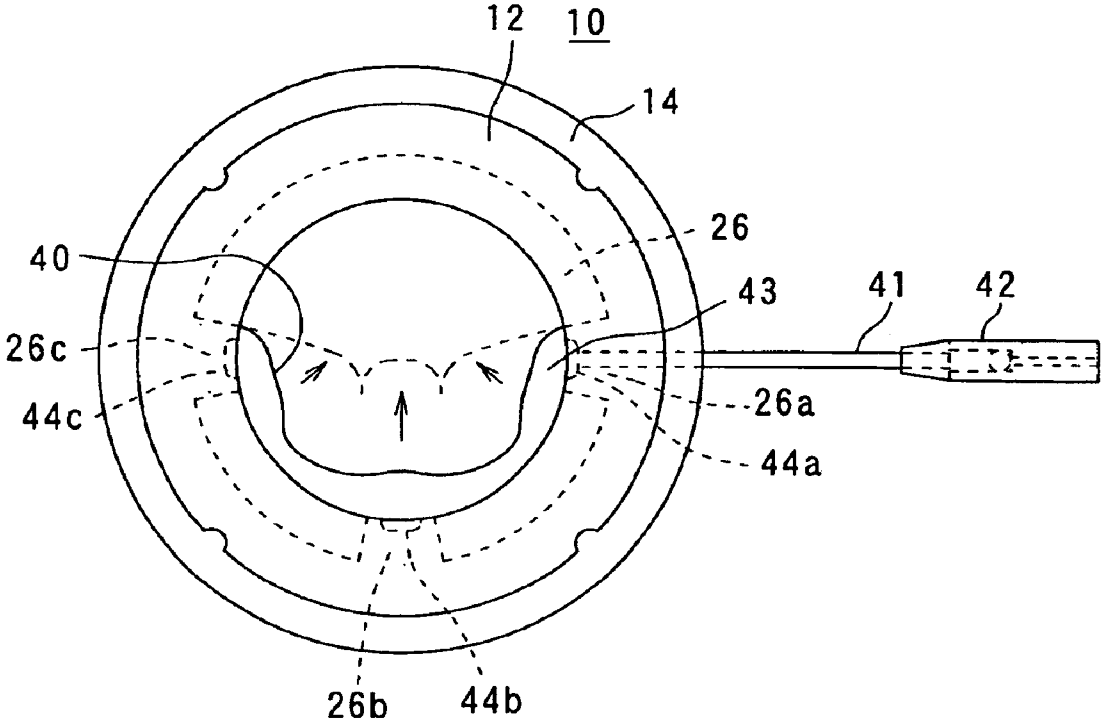
FIG. 7 shows a state of a sexually sensitive portion stimulating ring for the second embodiment of the present invention in which a hollow structural body is fitted on the inner side of the inner ring in the radial direction of the ring.

An embodiment in which a hollow structural body 40 has another configuration is shown in FIG. 7. The hollow structural body 40 of the embodiment has an inflating portion 43 which is hollow in its interior and inflates inward in the radial direction of the ring by injection of air and attachments 44*a*, 44*b*, and 44*c* for attaching this inflating portion 43 to the inside of the inner ring 12. The inner ring 12 forms holes to which the attachments 44*a*, 44*b*, and 44*c* are to be attached. As shown in the figure, the projection 26 formed with the outer ring 14 forms notches 26*a*, 26*b*, and 26*c* for reserving spaces to which the attachments 44*a*, 44*b*, and 44*c* is installed.

Among the three attachments 44*a*, 44*b*, and 44*c* of the hollow structural body 40, only the attachment 44*a* have an open mouth. One end of the hose 41 are attached to the open mouth of the attachment 44 by bonding and fixing or the like. The hose 41 is attached to the open mouth of the attachment 44*a* through a groove which is formed on the both thick-walled portions 20 of the outer ring 14 and is not illustrated in the figure, a side of ring-shape keeping member 30, and a hole which is formed with the curved portion 22 of the outer ring 14 and is not illustrated in the figure.

With the configuration shown above, when a user attaches the air pump 50 to the air injecting portion 42 at the other end of the hose 41 and operate the air pump 50, air is supplied to the interior of the hollow structural body 40 from the air pump 42 through the air injecting portion 42 and the hose 41, the inflating portion 43 inflates toward the direction of the arrow in the figure, and the inflating portion 43 comes to the state shown by the broken line in the figure.

Figure 8A:
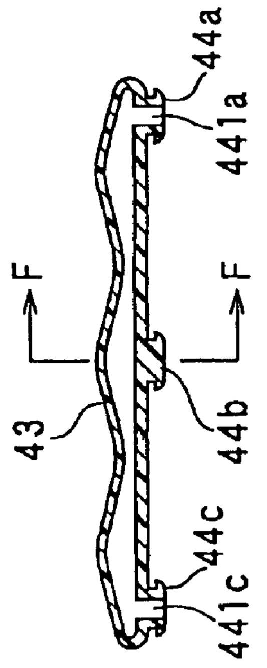
FIG. 8 shows a concrete configuration of the hollow structural body shown in FIG. 7.
Figure 8B:
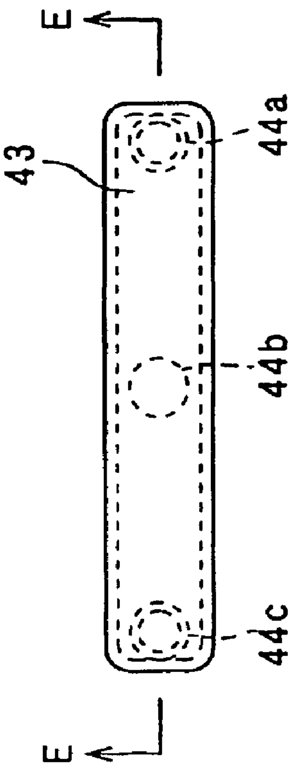
Figure 8C:

A concrete configuration of the hollow structural body 40 is shown in FIG. 8. FIG. 8(*a*) is a sectional view of FIG. 8(*b*) taken along the E—E line, FIG. 8(*b*) is a top view, and FIG. 8(*c*) is a sectional view of FIG. 8(*b*) taken along the F—F line. The hollow structural body 40 is formed of a material body (for example, elastic member like silicone rubber) which inflates by injection of air, and its upper surface has a geometry of waveform so that the inflating portion 43 inflates easily. In forming the hollow structural body, open mouths 441*a* and 441*c* are formed the attachments 44*a* and 44*c* respectively because of limitation in formation, but the open mouth 441*c* at the attachment 44*c* is sealed by replenishment member not illustrated in the figure to inject air only from the attachment 44.

In the first and second embodiment described above, it is possible to make the operation of injecting air into the hollow structural body 40 easy because the hose 41 is attached to the hollow structural body 40 beforehand, but the sexually sensitive portion stimulating ring 10 may have such a configuration that air injection is done by inserting a nozzle into the hollow structural body 40 and the air injected is kept within it after pulling out the nozzle.

Moreover, In the first and second embodiment described above, the sexually sensitive portion stimulating ring 10 in which the inner ring 12 and the outer ring 14 comprise the ring body separately is shown, but the ring body can be comprised unitedly if distance between its peripheral portions in the radial direction of the ring vary with change of pressure from its sides (Third Embodiment)

Hereafter, a sexually sensitive portion stimulating ring 10 according to the third embodiment of the present invention is described. Because the fundamental configuration of that is basically same as that shown in FIG. 1 and FIG. 2, its parts which differ from the ones in FIGS. 13–15 will mainly be described.

Figure 9B:
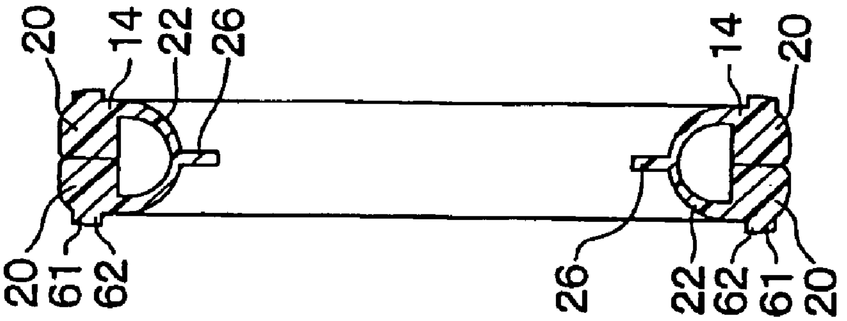
FIG. 9 shows a configuration of the outer ring of a sexually sensitive portion stimulating ring for the third embodiment of the present invention.
Figure 9A:
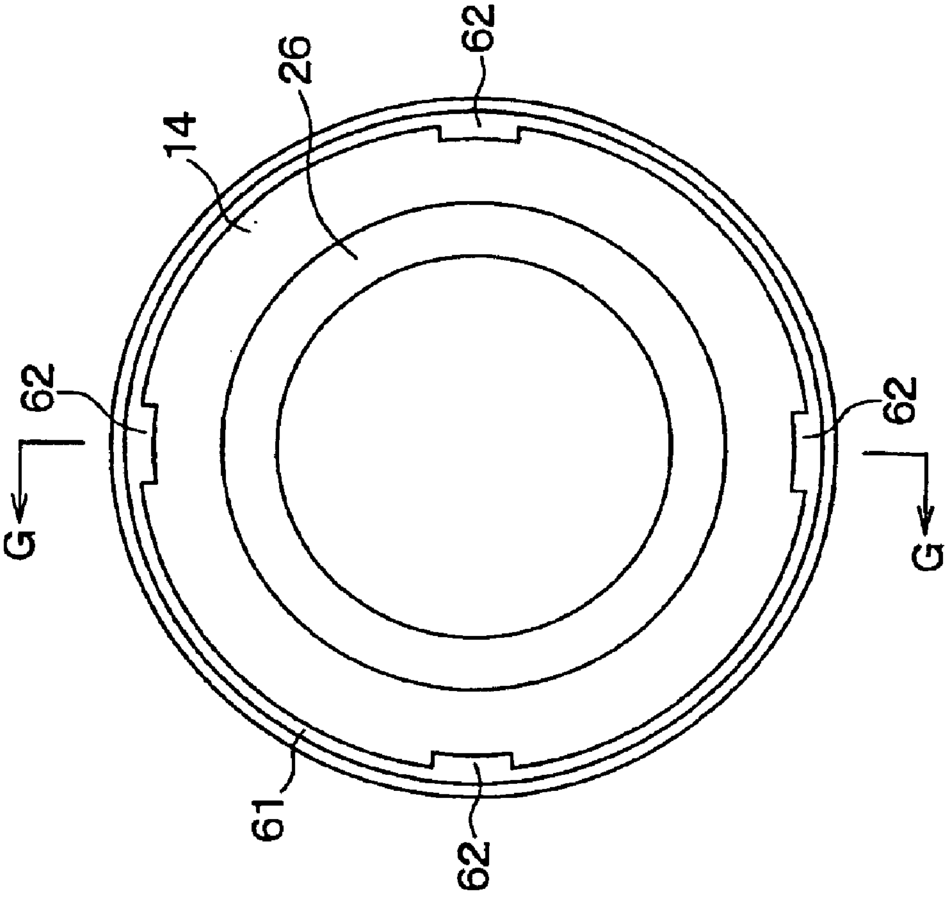
Figure 10B:
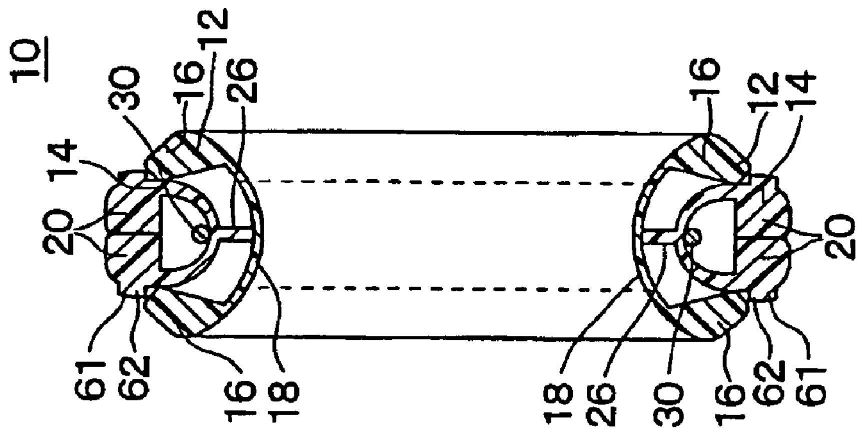
FIG. 10 shows a state of a sexually sensitive portion stimulating ring for the third embodiment of the present invention in which the outer ring is fitted on the inner ring.
Figure 10A:
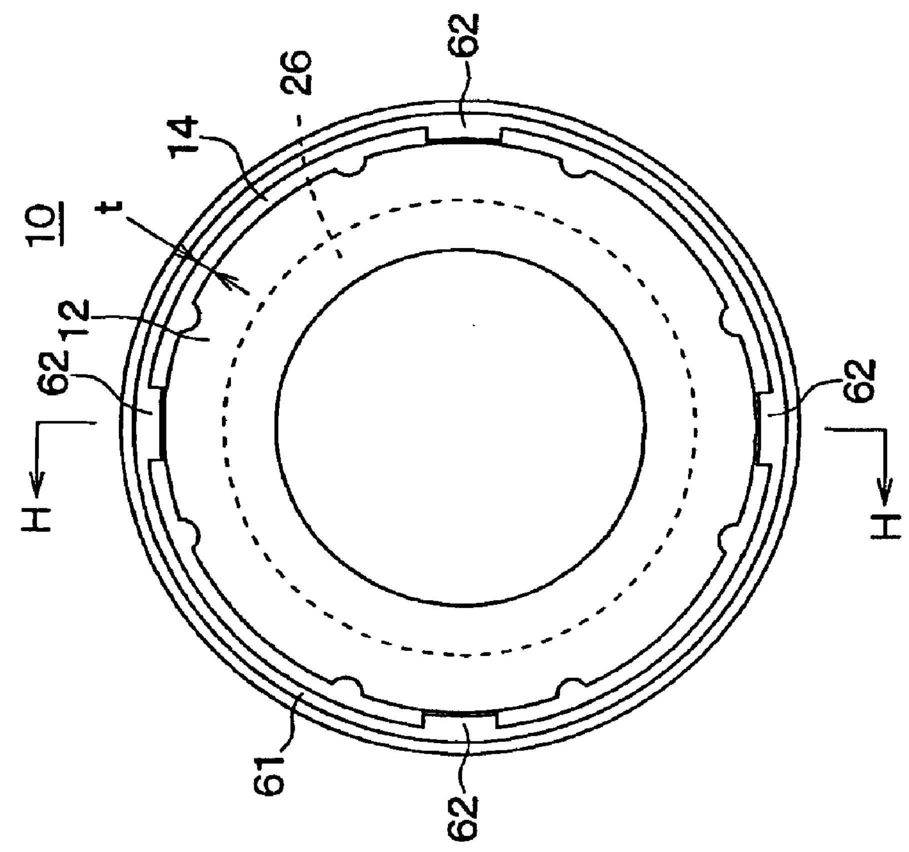

Configuration of the outer ring 14 in this embodiment is shown in FIG. 9. FIG. 9(*a*) is a side view of the outer ring 14, and FIG. 9(*b*) is a sectional view taken along the line G—G of FIG. 9(*a*). A state in which the outer ring 14 is fitted on the inner ring 12 is shown in FIG. 10. FIG. 10(a) is a side view thereof, and FIG. 10(*b*) is a sectional view taken along the line H—H of FIG. 10(*a*).

In this embodiment, as shown in FIG. 9, a circular salient 61 is formed on the surface of each outside (outside in the widthwise direction of the ring) of the both thick-walled portions 20 of the outer ring 14. Flanges 62 are formed on several point symmetric positions, for example on upper, lower, left, and right positions inside (inside in the radial direction) the salient 61. The salient 61 and the flanges 62 are formed unitedly with the outer ring 14.

As shown in FIG. 10, when the outer ring 14 as above is fitted on the inner ring 12, the outermost portion of the inner ring 12 contacts the flanges 62 formed on the four positions inside the salient 61. Consequently, during sexual intercourse, it is possible to prevent the outer ring 14 and the inner ring 12 from slipping off each other. This flange 62 contacts the outermost portion of the inner ring at a plurality of points and comprises slipping off preventing members which prevent the outer ring 14 and the inner ring from slipping off each other.

Figure 11B:
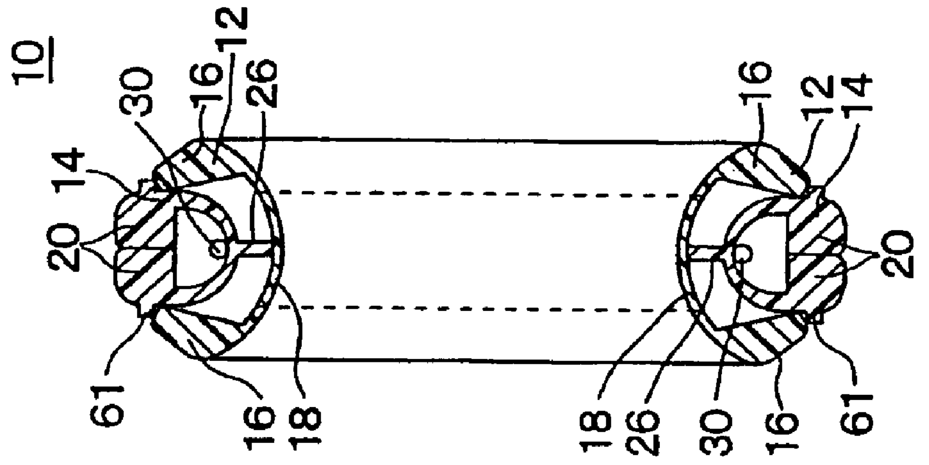
FIG. 11 shows another example of a sexually sensitive portion stimulating ring for the third embodiment of the present invention.
Figure 11A:
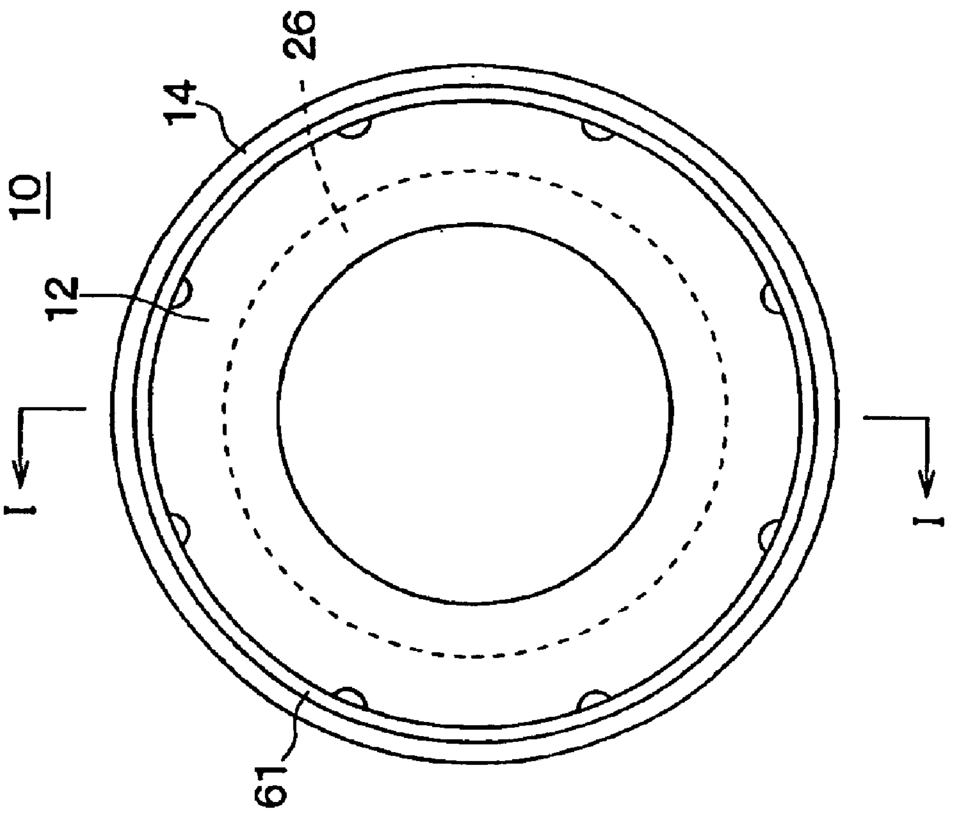

As shown in FIG. 11, the circular salient 61 which is formed on the outer surface of each thick-walled portion 20 may serve as the slipping off preventing member. Thus, when the outer ring 14 is fitted on the inner ring 12, the salient 61 comes in contact with the outermost part of the inner ring 12 circumferentially. In FIG. 11, FIG. 11(*a*) is a side view of a state in which the outer ring 14 is fitted on the inner ring 12, and FIG. 11(*b*) is a sectional view taken along the line I—I of FIG. 11(*a*). However, being constructed as above, the inner ring 12 would not be easy to displace during sexual intercourse. So in order to make the inner ring 12 easy to displace during sexual intercourse, it is preferable to shift the salient 61 by distance t toward the peripheral circumference, form the flanges 62 inside the salient 61 at plurality of points, and prevent the position gap with the flanges 62, as shown in FIG. 9 and FIG. 10. The flanges may count other than four.

In addition, by shifting the salient 61 toward the peripheral circumference, it is possible to improve a feeling of sexual pleasure given to a female. In other words it can be said as follows. In other words, a feeling of sexual pleasure is given to a female by the sexually sensitive portion stimulating ring 10 shown in FIG. 1 and FIG. 2 when the thick-walled portion 20 of the outer ring 14 makes a motion of spreading outward in the widthwise direction of the ring and as a result the radius of the peripheral portion of the outer ring 14 comes in contact with a female vulva, but in this occasion, if the salient 61 is formed as described above, the salient 61 also makes a motion of spreading outward in the widthwise direction of the ring and it is possible to improve the feeling of sexual pleasure given to the female.

In this case, as shown in FIG. 9 and FIG. 10, when the outer ring 14 is shifted toward more peripheral circumference of the ring 14 than that shown in FIG. 11, the feeling of sexual pleasure given to the female becomes more intense because the motion of spreading the salient 61 makes outward in the widthwise direction of the ring becomes larger.

In this embodiment, there are more grooves 16*a* formed on the surface inside the thick-walled potion 16 of the inner ring 12 than in the first embodiment, and as an example the number of the grooves 16*a* is eight and the number of the air holes 29 is eight. By increasing the number of the air holes 29 as above, during sexual intercourse, in addition to the effect that it is possible to quickly return both thick-walled portions 20 and 16 from the outwardly displaced state to the original state, it is possible to guide body fluids which spills over from a female sexual organ through the air holes 29 to within the curved portion 18 of the inner ring 12 and thus prevent inconvenience that the body fluid makes movements of the both thick-walled portions get worse.

Figure 12:
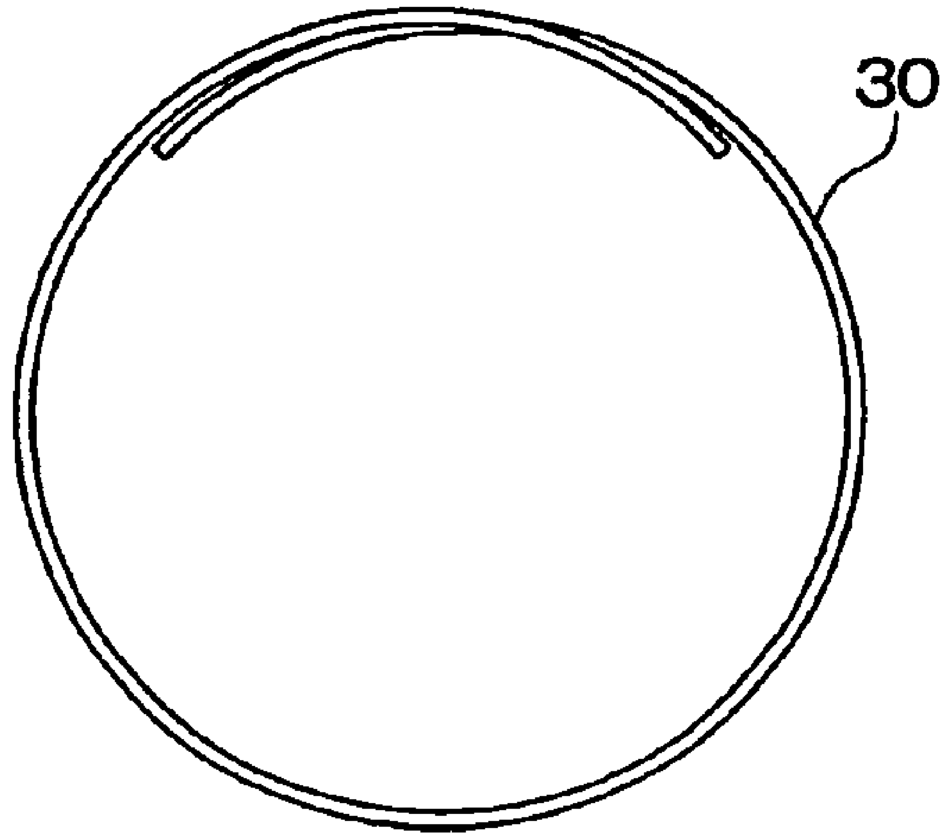
FIG. 12 shows a spring free at its both end which is used as the ring-shape keeping member.

In this embodiment, a spring 30 shown in FIG. 12 is used serving as a ring-shape keeping member 30. If the ring-shape keeping member 30 had a shape of closed loop, it would be possible to keep the shape of the outer ring 14 and the inner ring 12 circular but they would become hard to displace. In contrast, by using the spring 30 serving as the ring-shape keeping member 30 and making the spring 30 be free at its both end, it is possible to make the outer ring 14 and the inner ring 12 displace moderately as well as keep the shape of the outer ring 14 and the inner ring 12 circular.

The sexually sensitive portion stimulating ring 10 according to the third embodiment is used in the state shown in FIG. 10. The hollow structural body 40 described in the first and the second embodiment above can be used by attaching it inside the inner ring 12 in the radial direction of the ring.

(Other Embodiments)

It is possible to prepare a plurality of the sexually sensitive portion stimulating rings having different sizes in the inner diameter of the ring, the outer diameter thereof, and the width thereof. In this case, it is possible to appropriately select a sexually sensitive portion stimulating ring having a suitable size, according to a difference among individuals such as the thickness of the penis.

It is possible to prepare silicone rubber having different levels of hardness. In this case, it is possible to select a desired hardness.

What is claimed is:

1. A ring-shaped sexually sensitive portion stimulating tool which is fitted on a penis root, comprising:

a ring body elastically deformable;

a first displacement portion which is provided on said ring body and is displaced elastically to an inner side in a widthwise direction of said ring body when said ring body is pressed in said widthwise direction of said ring body; and a second displacement portion which is provided on said ring body and is displaced to an outer side in said widthwise direction of said ring body with a displacement of said first displacement portion to said inner side in said widthwise direction of said ring body, wherein said second displacement portion is constructed as a female sexual organ stimulating portion, said sexually sensitive portion stimulating tool further comprising a hollow structural body which is provided on an inner side of said ring body in a radial direction thereof and inflates inward in said radial direction.

2. A sexually sensitive portion stimulating tool according to claim 1, wherein said second displacement portion makes a motion of displacing outward in said widthwise direction of said ring body, while said second displacement portion is displacing outward in said radial direction of said ring body.

3. A sexually sensitive portion stimulating tool according to claim 1 or 2, wherein a peripheral portion of said second displacement portion makes a motion of spreading outward in said widthwise direction of said ring body, with an inner peripheral portion of said second displacement portion in said radial direction of said ring body serving as a supporting point.

4. A ring-shaped sexually sensitive portion stimulating tool which is fitted on a penis root, comprising:

a ring body elastically deformable;

wherein said ring body comprising:

an inner ring, approximately U-shaped in section, having a groove open in a peripheral direction thereof; and an outer ring which has a female sexual organ stimulating portion and is fitted in said groove of said inner ring, wherein when said inner ring deforms elastically upon receipt of a pressing force from opposite sides thereof in a widthwise direction of said ring body, said inner ring presses said outer ring, thus moving said female sexual organ stimulating portion, said sexually sensitive portion stimulating tool further comprising a hollow structural body which is provided on an inner side of said inner ring in a radial direction thereof and inflates inward in said radial direction.

5. A ring-shaped sexually sensitive portion stimulating tool which is fitted on a penis root, comprising:

an outer ring, approximately U-shaped in section, having a pair of thick-walled portions whose inner-side surfaces confront each other and a curved portion connecting said both thick-walled portions to each other; and an inner ring, approximately U-shaped in section, having a groove open in a peripheral direction thereof, wherein said outer ring is fitted in said groove of said inner ring; and upon receipt of a pressing force applied to an outer-side surface of said inner ring, both tips of said U-shaped inner ring press outer-side surfaces of said both thick-walled portions of said outer ring to allow each of said both thick-walled portions to make a rotary motion, with an end, at the side of said curved portion, of an inner-side surface of each of said both thick-walled portions of said outer ring operating as a supporting point so that said both thick-walled portions stimulate a female sexual organ, said sexually sensitive portion stimulating tool further comprising a hollow structural body which is provided on an inner side of said inner ring in a radial direction thereof and inflates inward in said radial direction.

6. A sexually sensitive portion stimulating tool according to claim 4 or 5, wherein a positioning member for keeping said outer ring having a constant distance with respect to said inner ring is provided inside said groove of said inner ring.

7. A sexually sensitive portion stimulating tool according to claim 6, wherein said positioning member is formed integrally with said outer ring.

8. A ring-shaped sexually sensitive portion stimulating tool which is fitted on a penis root, comprising:

an outer ring whose outer edge serves as a female sexual organ stimulating portion; and an inner ring whose side surface receives a pressing force, said sexually sensitive portion stimulating tool further comprising a stepped construction in such a way that when said sexually sensitive portion stimulating tool is seen from a peripheral surface side thereof, said inner ring is positioned at an outer side in a widthwise direction of said sexually sensitive portion stimulating tool and said outer ring is positioned at an inner side in said widthwise direction thereof, and said outer ring is positioned outward beyond said inner ring in a radial direction of said sexually sensitive portion stimulating tool to form a stepped construction, wherein said female sexual organ stimulating portion displaces outward in said widthwise direction of said sexually sensitive portion stimulating tool upon receipt of a pressing force applied to said side surface of said inner ring and stimulates a female sexual organ, said sexually sensitive portion stimulating tool further comprising a hollow structural body which is provided on an inner side of said inner ring in a radial direction thereof and inflates inward in said radial direction.

9. A ring-shaped sexually sensitive portion stimulating tool which is fitted on a penis root, comprising:

a ring body having a first ring portion; a second ring portion parallel with said first ring portion in a widthwise direction of said sexually sensitive portion stimulating tool; and an elastically deformable holding portion for holding said first and second ring portions, wherein said ring body is so formed that a distance between a peripheral portion of said first ring portion and that of said second ring portion in a radial direction of said sexually sensitive portion stimulating tool is varied by a change in a pressing force applied to a side surface of said sexually sensitive portion stimulating tool, said sexually sensitive portion stimulating tool further comprising a hollow structural body which is provided on an inner side of said ring body in a radial direction thereof and inflates inward in said radial direction.

10. A sexually sensitive portion stimulating tool according to claim 9, wherein said holding portion is positioned at an inner peripheral side of said first and second ring portions in said radial direction of said sexually sensitive portion stimulating tool and supports said first and second ring portions at a thin-walled portion thereof thinner than said first and second ring portions; and said thin-walled portion supports said first and second ring portions at a side surface thereof opposite to confronting side surfaces of said first and second ring portions.

11. A sexually sensitive portion stimulating tool according to claim 10, wherein said hollow structural body inflates by injection of air.

12. A sexually sensitive portion stimulating tool according to claim 11, wherein a hose which has air injecting portion is attached to said hollow structural body.

13. A ring-shaped sexually sensitive portion stimulating tool which is fitted on a penis root, comprising:

an outer ring whose outer edge serves as a female sexual organ stimulating portion; and an inner ring whose side surface receives a pressing force, said sexually sensitive portion stimulating tool further comprising a stepped construction in such a way that when said sexually sensitive portion stimulating tool is seen from a peripheral surface side thereof, said inner ring is positioned at an outer side in a widthwise direction of said sexually sensitive portion stimulating tool and said outer ring is positioned at an inner side in said widthwise direction thereof, and said outer ring is positioned outward beyond said inner ring in a radial direction of said sexually sensitive portion stimulating tool to form a stepped construction, wherein said female sexual organ stimulating portion displaces outward in said widthwise direction of said sexually sensitive portion stimulating tool upon receipt of a pressing force applied to said side surface of said inner ring and stimulates a female sexual organ, said sexually sensitive portion stimulating tool further comprising slipping off preventing members, which are provided on opposite sides of said outer ring, wherein said slipping off preventing members contact corresponding outer circumferential portions of said inner ring.

14. A ring-shaped sexually sensitive portion stimulating tool which is fitted on a penis root, comprising:

an outer ring, approximately U-shaped in section, having a pair of thick-walled portions whose inner-side surfaces confront each other and a curved portion connecting said both thick-walled portions to each other; and an inner ring, approximately U-shaped in section, having a groove open in a peripheral direction thereof, wherein said outer ring is fitted in said groove of said inner ring; and upon receipt of a pressing force applied to an outer-side surface of said inner ring, both tips of said U-shaped inner ring press outer-side surfaces of said both thick-walled portions of said outer ring to allow each of said both thick-walled portions to make a rotary motion, with an end, at the side of said curved portion, of an inner-side surface of each of said both thick-walled portions of said outer ring operating as a supporting point so that said both thick-walled portions stimulate a female sexual organ, said sexually sensitive portion stimulating tool further comprising slipping of preventing members, which are provided on opposite sides of said outer ring, wherein said slipping off preventing members contact corresponding outer circumferential portions said inner ring.

15. A ring-shaped sexually sensitive portion stimulating tool which is fitted on a penis root, comprising:

an elastically deformable ring body, said ring body comprising:

an inner ring, approximately U-shaped in section, having a groove open in a peripheral direction thereof; and an outer ring which has a female sexual organ stimulating portion and is fitted in said groove of said inner ring, wherein when said inner ring deforms elastically upon receipt of a pressing force from opposite sides thereof in a widthwise direction of said ring body, said inner ring presses said outer ring, thus moving said female sexual organ stimulating portion, said sexually sensitive portion stimulating tool further comprising slipping off preventing members, which are provided on opposite sides of said outer ring, wherein said slipping off preventing members contact corresponding outer circumferential portions of said inner ring.

16. A sexually sensitive portion stimulating tool according to claim 15 or 14, wherein a positioning member for keeping said outer ring having a constant distance with respect to said inner ring is provided inside said groove of said inner ring.

17. A sexually sensitive portion stimulating tool according to claim 16, wherein said positioning member is formed integrally with said outer ring.

18. A sexually sensitive portion stimulating tool according to any one of claims 15, 14 and 13, wherein is circular salients are formed on the outer opposite sides of said outer ring said slipping off preventing members are formed on the inner side of said circular salients in the radial direction thereof.

19. A sexually sensitive portion stimulating tool according to any one of claims 15, 14 and 13, comprising a ring-shape keeping member in said outer ring.

20. A sexually sensitive portion stimulating tool according to claim 19, wherein said ring-shape keeping member is a spring free at its both ends.

21. A sexually sensitive portion stimulating tool according to any one of claims 15, 14 and 13, wherein air holes are formed on a plurality of positions between said outer ring and said inner ring.

* * * * *